United States Patent [19]

Hertzsch

[11] Patent Number: 5,434,263

[45] Date of Patent: Jul. 18, 1995

[54] PROCESS FOR THE PREPARATION OF 2-ACYLAMINO-6-HALOPURINE FROM 2,9-DIACYLGUANINE

[75] Inventor: Winfried Hertzsch, Frankfurt am Main, Germany

[73] Assignee: Hoechst Aktiengesellschaft, Frankfurt am Main, Germany

[21] Appl. No.: 604,218

[22] Filed: Oct. 26, 1990

[30] Foreign Application Priority Data

Dec. 16, 1989 [DE] Germany .................. 39 41 657.7

[51] Int. Cl.$^6$ ............................................ C07D 473/40
[52] U.S. Cl. ................................... 544/264; 544/277
[58] Field of Search ..................................... 544/264

[56] References Cited

U.S. PATENT DOCUMENTS 4,405,781  9/1983  Bader et al. ......................... 544/264
4,736,029  4/1988  Harnden et al. ...................... 544/277

FOREIGN PATENT DOCUMENTS 0203685  12/1986  European Pat. Off. .

OTHER PUBLICATIONS

Bendich et al, J. Am. Chem. Soc. vol. 76, 6073–6077, 1954.
W. A. Bowles et al., J. Med. Chem. 6, 1963, pp. 471–480.
H. Hrebabecky et al., Nucleic Acid Chemistry, 1978, pp. 13–14.

*Primary Examiner*—Yogendra N. Gupta
*Attorney, Agent, or Firm*—Finnegan, Henderson, Farabow, Garrett & Dunner

[57] ABSTRACT

2-Acylamino-6-halopurine can be prepared by halogenation of 2,9-diacylguanine (2-acylamino-6-oxo-9-acylpurine) with phosphorus oxychloride or phosphorus oxybromide in the presence of a base and of a salt with subsequent hydrolysis of the reaction product.

10 Claims, No Drawings

PROCESS FOR THE PREPARATION OF 2-ACYLAMINO-6-HALOPURINE FROM 2,9-DIACYLGUANINE

2-Acylamino-6-halopurines are widely employable intermediates for the pharmaceutical industry in the area of nucleoside syntheses.

2-Acetamido-6-chloropurine is a compound which is known in the literature. 2-Amino-6-oxopurine (guanine), for example, which is converted by means of chlorination to 2-amino-6-chloropurine with subsequent acetylation to 2-acetamido-6-chloropurine is used as a starting material for its synthesis. European Patent Application 0,203,685 describes a process for the preparation of 2-amino-6-chloropurine from guanine. To this end, guanine is chlorinated at reflux temperature in acetonitrile together with phosphorus oxychloride and tetraethylammonium chloride. After continuous extraction for 24 hours, 2-amino-6-chloropurine is obtained with a yield of 42%. The use of acetic anhydride in N,N-dimethylacetamide for the acetylation of 2-amino-6-chloropurine to 2-acetamido-6-chloropurine is described by W. A. Bowles et al. (J. Med. Chem. 4, 1963, 471–480). In this case, a yield of 44% is achieved at 150° C. The synthesis route from 2-acetamido-6-chloropurine, which starts from guanine and leads via 2-amino-6-chloropurine, is associated with high yield losses and characterized by long extraction times.

Surprisingly, it has now been found that 2-acylamino-6-halopurine can be prepared in high yields by halogenation of 2,9-diacylguanine (2-acylamino-6-oxo-9-acylpurine). The invention thus relates to a process for the preparation of the compound of the formula I

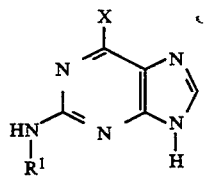

in which $R^1$ is a straight-chain or branched acyl group having 2 to 10 carbon atoms or an aroyl group having 7 to 10 carbon atoms and X is chlorine or bromine, which 5 comprises reacting 2,9-diacylguanine of the formula II

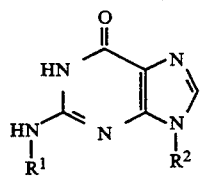

in which $R^1$ and $R^2$, which can be the same or different, are a straight-chain or branched acyl group having 2 to 10 carbon atoms or an aroyl group having 7 to 10 carbon atoms, with a halogenating agent in the presence of a base and of a salt and hydrolyzing the reaction product.

The invention is described in detail in the following, in particular in its preferred embodiments.

The described acyl groups having 2 to 10 carbon atoms are understood as meaning, for example, the radicals of the following acids: acetic acid, propionic acid, n-butyric acid, i-butyric acid, n-valeric acid, i-valeric acid, methylethylacetic acid, trimethylacetic acid, caproic acid, caprylic acid, capric acid, heptanoic acid and nonanoic acid. The description aroyl group having 7 to 10 carbon atoms means, for example, the radicals of the following compounds: benzoic acid, phenylacetic acid, phenylpropanoic acid, phenyl-n-butyric acid or phenyl-i-butyric acid.

The preparation of the compound of the formula I according to the invention starts from 2,9-diacylguanine (2-acylamino-6-oxo-9-acylpurine). To this end, 2,9-diacylguanine can be suspended in a polar inert solvent, such as acetonitrile, tetrahydrofuran, dioxane, nitromethane or dimethoxyethane. A suitable base, such as, for example, triethylamine, N-ethylpiperidine or N,N-dimethylaniline is then added. The molar ratio of base to 2,9-diacylguanine is expediently 1–6 to 1, preferably 1–2 to 1.

A suitable alkyl halide salt is then added, such as, for example, tetraethylammonium chloride, triethylamine hydrochloride, tetraethylammonium bromide, tetramethylammonium chloride, tetramethylammonium bromide, tetrabutylammonium bromide or tetrabutylammonium chloride. The molar ratio of alkyl halide salt to 2,9-diacylguanine is 1–3 to 1, preferably 1.5–2 to 1.

A halogenating agent such as phosphorus oxychloride or phosphorus oxybromide is then added. The molar ratio of halogenating agent to 2,9-diacylguanine is 1–10 to 1, preferably 4–6 to 1. The halogenating agent is added in a temperature range from −10° C. to 30° C., preferably between 0° C. and 5° C. After addition of the halogenating agent, the temperature of the reaction mixture is kept between 10° C. and 80° C., preferably between 15° C. and 30° C. The reaction time is 10 minutes to 72 hours, preferably 6 to 48 hours.

The sequence of the individual process steps can also be varied. A person skilled in the art does not find it difficult to find the optimum sequence for the reaction process.

The reaction course is monitored by taking samples and by quantitative analysis of the resulting 2-acylamino-6-halo-9-acylpurine with the aid of high pressure liquid chromatography (HPLC).

The acyl group in position 9 of the purine ring is hydrolyzed, for example, by introducing the reaction mixture into water. The reaction product (2-acylamino-6-halo-9-acylpurine) is thereby hydrolyzed to the compound of the formula I. The temperature is kept between −10° C. and 30° C., preferably between 0° C. and 5° C. At the same time, the pH of the solution is set between 3 and 8, preferably between 4 and 7, using a suitable base. Suitable bases are, for example, ammonia solution, sodium hydroxide, potassium hydroxide, sodium carbonate, potassium carbonate, calcium hydroxide, sodium hydrogencarbonate or potassium hydrogencarbonate. 12% strength ammonia solution, 2N sodium carbonate solution or 2N sodium hydroxide solution are preferably used.

After a constant pH has been established, the reaction mixture is additionally further stirred. The temperature of the mixture is kept between −10° C. and 25° C., preferably between −5° C. and 5° C. It is stirred for between 0.5 and 24 hours, preferably between 1 and 10 hours. The compound of the formula I can then be obtained from the reaction mixture in high purity by filtration.

The preparation of 2,9-diacetylguanine (2-acetamido-6-oxo-9-acetylpurine) from guanine by acetylation has already been described (H. Hrebabecky, J. Farkas, Nucleic Acid Chemistry, 1978, 13–14). In this process, guanine is acetylated to N-methyl-2-pyrrolidone using acetic anhydride. Homologous 2,9-diacylguanines can be obtained in an analogous manner.

In comparison to the routes for the synthesis of 2-acylamino-6-halopurines known hitherto, the process according to the invention opens up the advantage of obtaining the final product in high purity and yield. As the final product can be obtained directly from the reaction solution by filtration, lengthy extraction processes are also avoided.

EXAMPLE 1

45.0 g (0.27 mol) of tetraethylammonium chloride and 22.8 g (0.2 mol) of N-ethylpiperidine are added to a suspension of 42.6 g (0.18 mol) of 2,9-diacetylguanine in 450 ml of acetonitrile. 165.3 g (1.08 mol) of phosphorus oxychloride are then metered in at a temperature of 0° C. to 5° C. of the reaction mixture. The mixture is stirred at 25° C. for 20 hours, then introduced into 1.25 l of water such that 15° C. is not exceeded and the pH is at the same time kept between 4.8 and 5.5 using 12% strength ammonia solution. The mixture is stirred at 0° C. to 5° C. for 1 hour at a constant pH of 5, then the product is filtered off, washed with water and dried in vacuo at 50° C. 34.1 g of 2-acetamido-6-chloropurine are obtained. The final product is determined with the aid of HPLC on an RP-18 column in a reaction mixture of water, acetonitrile and acetic acid in the ratio 6:1:0.5.

Yield: 87.3% of theory Purity: 97.2% (HPLC)

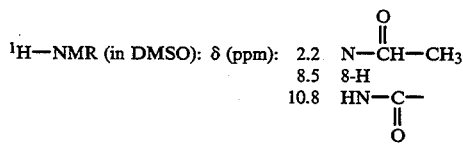

$^1$H—NMR (in DMSO): δ (ppm): 2.2 N—CH—CH$_3$
8.5 8-H
10.8 HN—C—
             ‖
             O

EXAMPLE 2

60.0 g (0.36 mol) of tetraethylammonium chloride and 20.3 g (0.2 mol) of triethylamine are added to a suspension of 42.6 g (0.18 mol) of 2,9-diacetylguanine in 450 ml of acetonitrile. 165.3 g (1.08 mol) of phosphorus oxychloride are then added at a temperature of the reaction mixture of 0° C. to 5° C. The mixture is stirred at 25° C. for 20 hours and then worked up as in Example 1. 30.9 g of 2-acetamido-6-chloropurine are obtained.

Yield: 80.6% of theory Purity: 99.1% (HPLC) $^1$H-NMR (see Example 1)

EXAMPLE 3

49.8 g (0.36 mol) of triethylamine hydrochloride and 20.3 g (0.2 mol) of triethylamine are added to a suspension of 42.6 g (0.18 mol) of 2,9-diacetylguanine in 450 ml of acetonitrile. 165.3 g (1.08 mol) of phosphorus oxychloride are metered into the reaction mixture at a temperature of 0° C. to 5° C. The mixture is stirred at 25° C. for 42 hours and then worked up as in Example 1. 25.1 g of 2-acetamido-6-chloropurine are obtained.

Yield: 64.5% of theory Purity: 97.6% (HPLC) $^1$H-NMR (see Example 1)

I claim:

1. A process for the preparation of the compound of the formula I

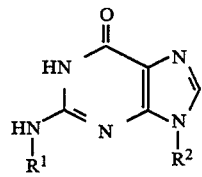

in which R$^1$ is a straight-chain or branched acyl group having 2 to 10 carbon atoms or an aroyl group having 7 to 10 carbon atoms and X is chlorine or bromine, which comprises reacting 2,9-diacylguanine of the formula II

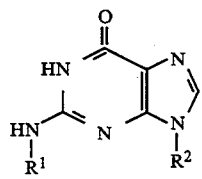

in which R$^1$ and R$^2$, which can be the same or different, are a straight-chain or branched acyl group having 2 to 10 carbon atoms or an aroyl group having 7 to 10 carbon atoms, with a halogenating agent in the presence of a base and of a salt and hydrolyzing the reaction product.

2. The process as claimed in claim 1, wherein phosphorus oxychloride or phosphorus oxybromide is used as the halogenating agent.

3. The process as claimed in claim 1, wherein N,N-dimethylaniline, N-ethylpiperidine or triethylamine is used as a base and triethylamine hydrochloride, tetrabutylammonium chloride, tetraethylammonium bromide, tetramethylammonium chloride, tetramethylammonium bromide, tetrabutylammonium bromide or tetraethylammonium chloride is used as a salt.

4. The process as claimed in claim 1, wherein the reaction is carried out at a temperature between −10° C. and 80° C.

5. The process as claimed in claim 1, wherein the molar ratio of halogenating agent to the compound of the formula II is 1–10 to 1.

6. The process as claimed in claim 5, wherein the molar ratio is 4–6 to 1.

7. The process as claimed in claim 1, wherein the molar ratio of salt to the compound of the formula II is 1–3 to 1.

8. The process as claimed in claim 1, wherein the molar ratio of base to the compound of the formula II is 1–6 to 1.

9. The process as claimed in claim 1, wherein the hydrolysis is carried out at a pH between 3 and 8.

10. The process as claimed in claim 9, wherein the hydrolysis is carried out at a temperature between −10° C. and 30° C.

* * * * *

UNITED STATES PATENT AND TRADEMARK OFFICE
CERTIFICATE OF CORRECTION

PATENT NO. : 5,434,263
DATED      : July 18, 1995
INVENTOR(S) : Winfried HERTZSCH It is certified that error appears in the above-indentified patent and that said Letters Patent is hereby corrected as shown below:

Claim 1, Column 4, at line 6, delete Formula I and insert therefor -- 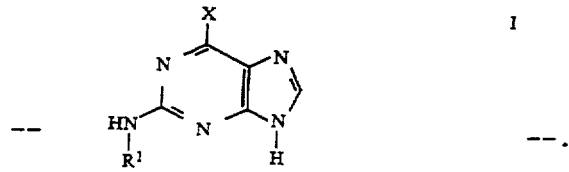 --.

Claim 1, Column 4, at line 20, delete Formula II and insert therefor -- 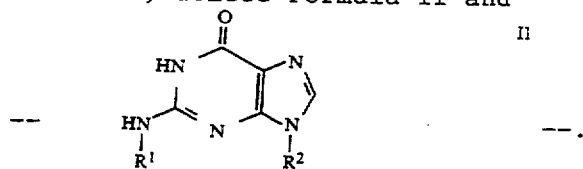 --.

Signed and Sealed this

Twenty-fourth Day of September, 1996

Attest:

BRUCE LEHMAN

Attesting Officer

Commissioner of Patents and Trademarks